(12) United States Patent
Masumoto et al.

(10) Patent No.: US 8,634,609 B2
(45) Date of Patent: Jan. 21, 2014

(54) APPARATUS FOR ACQUIRING A DIAGNOSTIC INDEX FOR BODY FAT

(75) Inventors: Jun Masumoto, Ichikawa (JP); Masaki Miyamoto, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 896 days.

(21) Appl. No.: 12/181,899

(22) Filed: Jul. 29, 2008

(65) Prior Publication Data

US 2009/0034815 A1     Feb. 5, 2009

(30) Foreign Application Priority Data

Jul. 30, 2007 (JP) ................................. 2007-197005

(51) Int. Cl.
*G06K 9/00* (2006.01)

(52) U.S. Cl.
USPC ........................................................ 382/128

(58) Field of Classification Search
USPC ........................................................ 382/128
See application file for complete search history.

(56) References Cited

U.S. PATENT DOCUMENTS

| | | | |
|---|---|---|---|
| 6,766,272 B2 | 7/2004 | Serita | |
| 2007/0038151 A1* | 2/2007 | Jang et al. | 600/587 |
| 2007/0299315 A1* | 12/2007 | Geller | 600/217 |
| 2009/0034815 A1* | 2/2009 | Masumoto et al. | 382/131 |
| 2010/0278405 A1* | 11/2010 | Kakadiaris et al. | 382/131 |
| 2011/0044524 A1* | 2/2011 | Wang et al. | 382/131 |
| 2011/0306884 A1* | 12/2011 | Tanigawa et al. | 600/443 |

FOREIGN PATENT DOCUMENTS

| | | | |
|---|---|---|---|
| JP | 2004-254933 A | | 9/2004 |
| JP | 2006034337 A | * | 2/2006 |
| JP | 2007105164 A | * | 4/2007 |

OTHER PUBLICATIONS

"Methods of Estimation of Visceral Fat: Advantages of Ultrasonography", Ribeiro-Filho, et al, Dec. 2003, obtained online at http://www.nature.com/oby/journal/v11/n12/pdf/oby2003199a.pdf.*
"A New Simple Method for the Measurement of Visceral Fat Accumulation by Bioelectrical Impedance", Ryo, et al, Feb. 2005, obtained online at http://care.diabetesjournals.org/content/28/2/451.full.pdf+html.*
"Abdominal Fat: Standardized Technique for Measurement at CT", Yoshizumi, et al, 1999, obtained online at http://radiology.rsna.org/content/211/1/283.full.pdf+html.*
Official Translation of JP2006-034337.*
Shuichi Okabe, Hiroshi Taniguchi, Mitsuru Denshu (Kobe University, School of Medicine, Faculty of Health Sciences), Kinuyo Matsumoto, Naemi Kajiwara (Kobe Women's University, Domestic Science), Yasutoshi Masuda (Himeji Institute of Technology, School of Engineering), "Relationship between the Areas of Visceral Fat for Respective Cross-Section levels of Abdomen by CT method and Obesity-Related Factors in Blood", Diabetes, Japan, Feb. 29, 2004, p. 181, vol. 47, No. 2.

(Continued)

*Primary Examiner* — Rodney Fuller
(74) *Attorney, Agent, or Firm* — Sughrue Mion, PLLC

(57) ABSTRACT

A diagnostic index that indicates a condition of obesity of an abdominal area of a human body with improved reliability is provided. For slice images representing two or more cross-sections of an abdominal area of a subject, a ratio of a size of the subcutaneous fat region and the visceral fat region in the abdominal area to the abdominal area is calculated. Then, the ratio obtained for the subject is compared with a corresponding ratio obtained in advance for a human body model to acquire the diagnostic index indicating the condition of obesity of the subject.

22 Claims, 5 Drawing Sheets

(56) References Cited

OTHER PUBLICATIONS

Japanese Office Action corresponding to Japanese Patent Application No. 2007-197005 dated Mar. 23, 2010.

Notice of Grounds for Rejection, dated Jul. 20, 2010, issued in corresponding JP Application No. 2007-197005, 4 pages in English and Japanese.

* cited by examiner

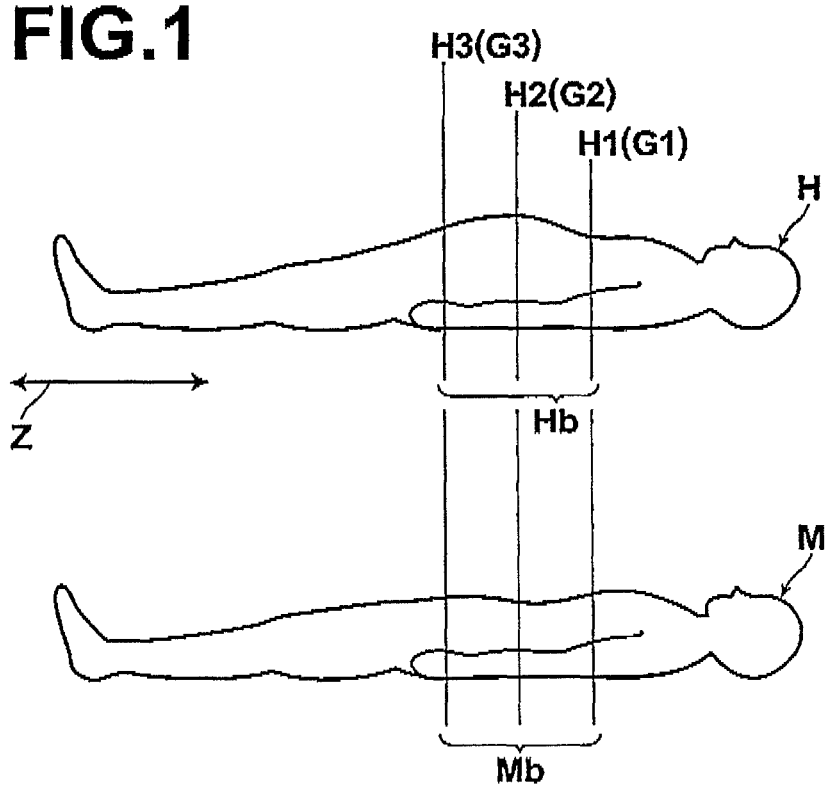

FIG. 3
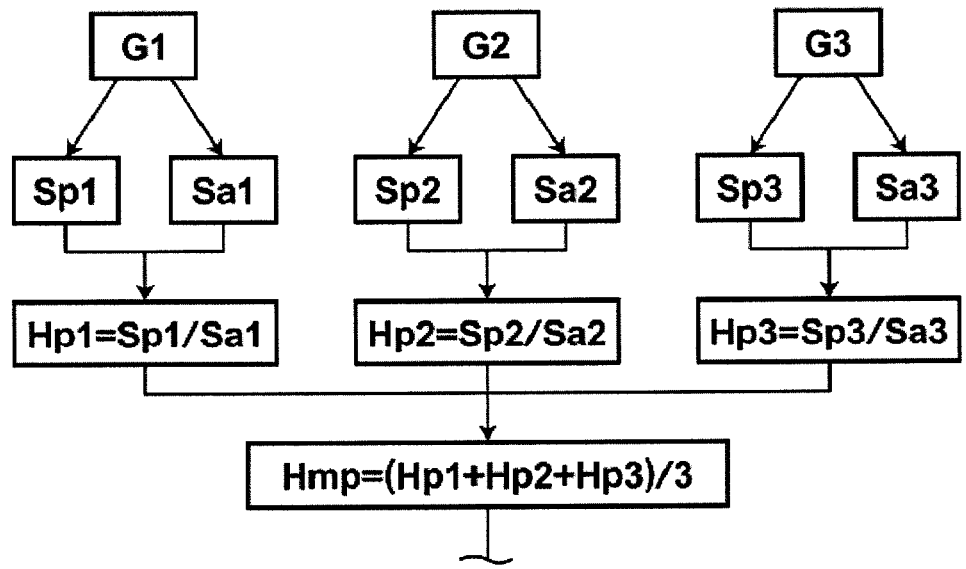
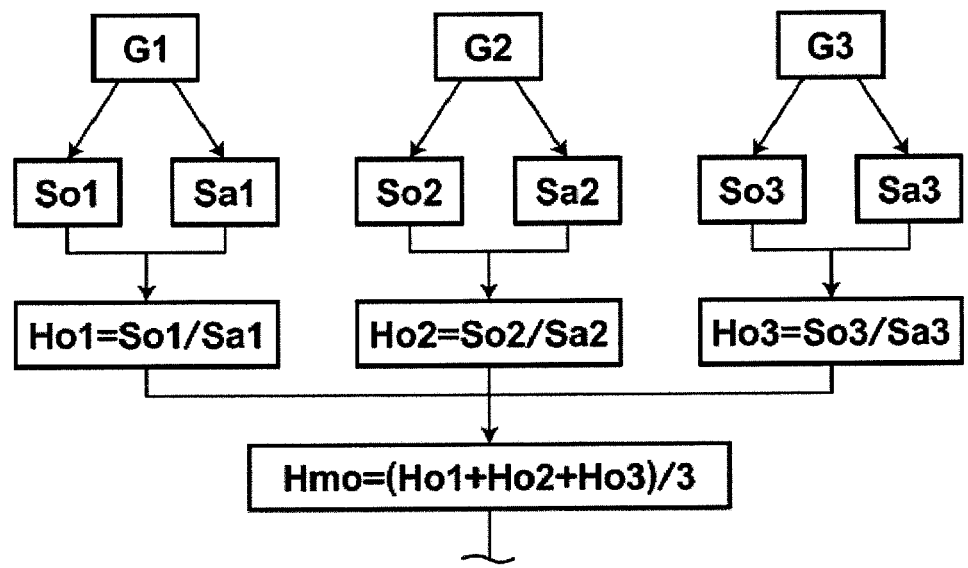

APPARATUS FOR ACQUIRING A DIAGNOSTIC INDEX FOR BODY FAT

BACKGROUND OF THE INVENTION

1. Field of the Invention

The present invention relates to a method of acquiring a diagnostic index, and in particular to a method of acquiring a diagnostic index that indicates a condition of obesity of a subject based on slice images of the abdominal area of the subject.

2. Description of the Related Art

Various techniques for measuring a body fat ratio indicating a ratio by weight of the body fat to the body weight have been known. Examples of such techniques to obtain the body fat ratio include: estimating the body fat ratio based on a body density that is obtained by measuring a difference between body weights of a subject human body under water and on land; and an impedance method in which the body fat ratio is estimated utilizing the fact that an electric resistance of a human body when a very small electric current flows therethrough varies depending on the amount of the body fat. It should be noted that the body fat is a collective term for fats forming a human body and includes the visceral fat and the subcutaneous fat.

Further, a technique for estimating a ratio of the visceral fat, which is a part of the body fat, to the human body is known (see Japanese Unexamined Patent Publication No. 2004-254933). In this technique, a slice image of a human body, which allows clear identification of a boundary of a visceral fat region, is obtained through tomographic imaging of the human body using a X-ray CT apparatus, and the ratio of the visceral fat to the human body is calculated from an area of the visceral fat region and an area of other regions in the slice image. In this technique, the visceral fat ratio is estimated from a single slice image that is taken along a plane crossing the umbilicus of the human body.

Furthermore, a technique for acquiring diagnosis information that indicates a condition of obesity of a subject is known. The diagnosis information is acquired based on areas of a visceral fat region and a subcutaneous fat region of the subject that are found from a singe slice image representing a cross-section of the abdominal area of the subject (see U.S. Pat. No. 6,766,272).

Since it is difficult to directly measure the body fat ratio, the visceral fat ratio and the subcutaneous fat ratio, these values are estimated indirectly from various measurement data, as described above.

There are differences among individuals in positional relationships between a cross-section of the abdominal area and the visceral organs of a subject, or between the cross-section and sites where the body fat tends to accumulate. Therefore, in a case where the diagnostic index is acquired from a slice image that represents a single cross-section taken along a plane crossing the umbilicus, a diagnostic index acquired for a certain subject and a diagnostic index acquired for another subject, whose diagnostic index should be similar to the diagnostic index of the first subject, may not be similar to each other. Thus, there is a demand for reduction of such discrepancy in the diagnostic indices due to differences in body structures of individual subjects.

SUMMARY OF THE INVENTION

In view of the above-described circumstances, the present invention is directed to providing a method of acquiring a diagnostic index which provides improved reliability of the diagnostic index indicating a condition of obesity of a subject.

The method of acquiring a diagnostic index of the invention acquires a diagnostic index with respect to body fat of a subject, the method includes: preparing slice images representing two or more cross-sections of an abdominal area of the subject; calculating, for each slice image, a ratio of a size of at least one of a subcutaneous fat region and a visceral fat region in the abdominal area to the abdominal area; and comparing the ratio obtained for the subject with a corresponding ratio obtained in advance for a human body model to acquire the diagnostic index indicating the condition of obesity of the subject.

It should be noted that the ratio obtained for the subject and the ratio obtained in advance for a human body model corresponds to each other. For example, if the ratio obtained for the subject is a ratio of sizes of the subcutaneous fat region and the visceral fat region in the abdominal area to the abdominal area of the subject, the ratio obtained in advance for the human body model is also the ratio of sizes of the subcutaneous fat region and the visceral fat region in the abdominal area to the abdominal area of the human body model.

The slice images may be taken more than once in time-series, and the diagnostic index may indicate a change in the condition of obesity over time.

The slice images may include a slice image representing a cross-section nearer to a head of the subject than a cross-section crossing an umbilicus of the subject and being orthogonal to a body height direction of the subject, and a slice image representing a cross-section nearer to legs of the subject than the cross-section crossing the umbilicus.

Each of the cross-sections of the abdominal area of the subject may be a cross-section that is orthogonal to a body height direction of the subject, or a cross-section that is oblique to the body height direction of the subject.

Further, the abdominal area of the subject may be an area between a cross-section that crosses any one of the periphery of the upper portion of the liver, the lower portion of the diaphragm and the intervertebral portion of the spine and is orthogonal to the body height direction of the subject, and a cross-section that crosses any one of the upper portion of the ilium bone, the lower portion of the ilium bone and the lower portion of the sacrum bone and is orthogonal to the body height direction of the subject.

BRIEF DESCRIPTION OF THE DRAWINGS

FIG. 1 illustrates positions of a subject and a human body model where slice images are taken in a method of acquiring a diagnostic index according to embodiments of the present invention, FIG. 3 is a first half of a flow chart of a process to acquire a diagnostic index indicating a condition of obesity of the subject from the slice images.

DESCRIPTION OF THE PREFERRED EMBODIMENTS

Hereinafter, a method of acquiring a diagnostic index according to embodiments of the present invention will be described.

Figure 2A:
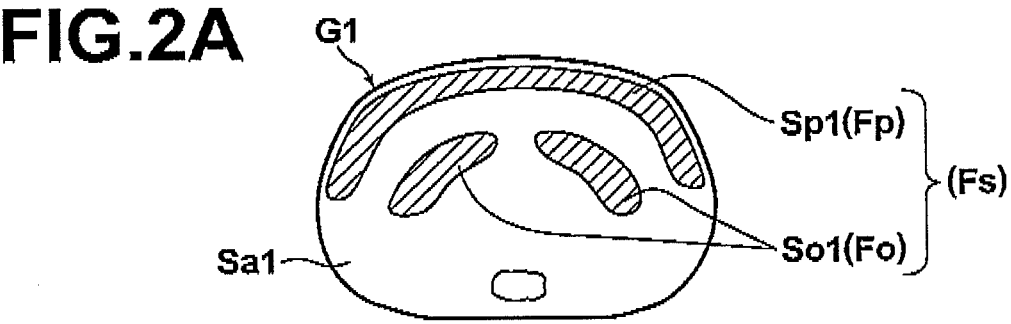
FIGS. 2A-2C illustrate slice images representing different cross-sections of an abdominal area.
Figure 2B:
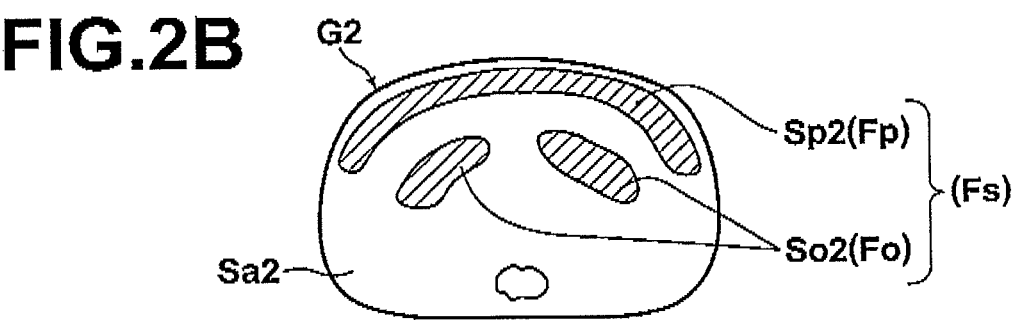
Figure 2C:
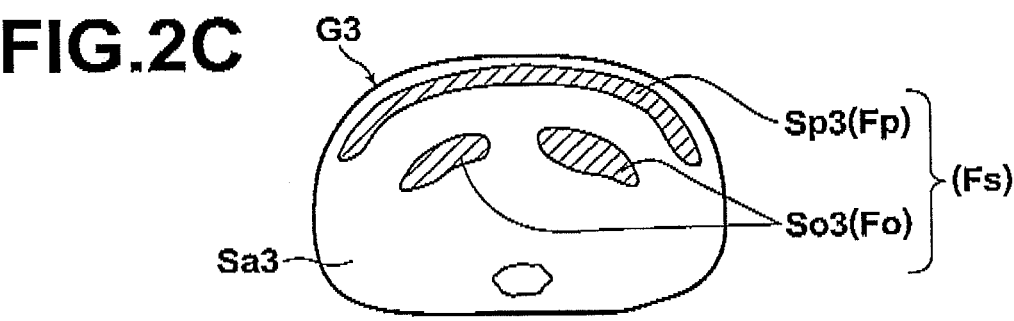
Figure 4:
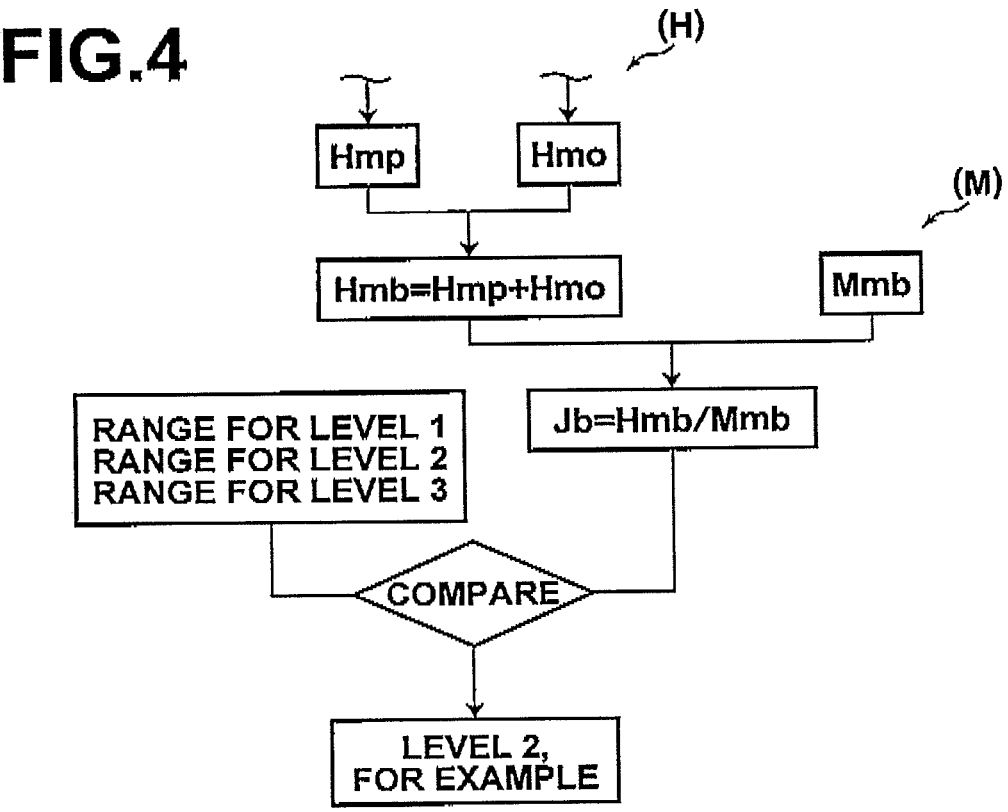
FIG. 4 is a second half of the flow chart of the process to acquire the diagnostic index indicating a condition of obesity of the subject from the slice images.

First, a first embodiment will be described. FIG. 1 illustrates positions of a subject and a human body model where slice images are taken, FIGS. 2A to 2C illustrate slice images taken along different cross-sections, FIG. 3 is the first half of a flow chart of a process to acquire a diagnostic index indicating a condition of obesity of a subject from the slice images, and FIG. 4 is the second half of the flow chart.

In the first embodiment of the method of acquiring a diagnostic index of the invention shown in the drawings, a diagnostic index (which may hereinafter be simply referred to as an "index") with respect to the body fat of a subject is acquired. In this embodiment, slice images representing two or more cross-sections of the abdominal area of the subject are prepared. For each slice image, ratios of sizes of a subcutaneous fat region and a visceral fat region in the abdominal area to the abdominal area are calculated, and these ratios of the subject are compared with the corresponding ratios of the human body model, which are obtained in advance, to acquire the index indicating a condition of obesity of the subject.

As shown in FIGS. 1, 2A, 2B and 2C, first, slice images G1-G3 representing three cross-sections H1-H3 of an abdominal area Hb of a subject H are prepared.

The slice images G1-G3 may be taken through tomographic imaging using an X-ray CT apparatus.

Then, subcutaneous fat region ratios Hp1-Hp3 are calculated. As shown in FIGS. 2A, 2B, 2C and 3, areas Sa1-Sa3 respectively represent sizes of the abdominal area Hb in the slice images G1-G3, areas Sp1-Sp3 respectively represent sizes of the subcutaneous fat region Fp within the abdominal area Hb in the slice images G1-G3, and the subcutaneous fat region ratios Hp1-Hp3 represent ratios of the areas Sp1-Sp3 to the areas Sa1-Sa3. The subcutaneous fat region ratios Hp1-Hp3 are calculated as follows:

$Hp1=Sp1/Sa1$, $Hp2=Sp2/Sa2$ and $Hp3=Sp3/Sa3$.

Then, an average Hmp of the subcutaneous fat region ratios Hp1, Hp2 and Hp3 is calculated as follows:

$Hmp=(Hp1+Hp2+Hp3)/3$.

Further, visceral fat region ratios Ho1-Ho3 are calculated. As shown in FIGS. 2A, 2B, 2C and 3, areas So1-So3 respectively represent sizes of the visceral fat region Fo in the abdominal area Hb in the slice images G1-G3, and the visceral fat region ratios Ho1-Ho3 represent ratios of the areas So1-So3 to the areas Sa1-Sa3. The visceral fat region ratios Ho1-Ho3 are calculated as follows:

$Ho1=So1/Sa1$, $Ho2=So2/Sa2$ and $Ho3=So3/Sa3$.

Then, an average Hmo of the visceral fat region ratios Ho1, Ho2 and Ho3 is calculated as follows:

$Hmo=(Ho1+Ho2+Ho3)/3$.

It should be noted that the subcutaneous fat region ratios Hp1-Hp3 and the visceral fat region ratios Ho1-Ho3 are values obtained by normalizing the sizes of the subcutaneous fat region and the visceral fat region in the individual slice images. That is, for each slice image, the size of the subcutaneous fat region and the size of the visceral fat region are respectively divided by the size of the abdominal area. The normalized subcutaneous fat region ratios and visceral fat region ratios each takes a value of zero or more and one or less.

Similarly, the average Hmp of the subcutaneous fat region ratios and the average Hmo of the visceral fat region ratios are values obtained by normalizing the sizes of the subcutaneous fat region and the visceral fat region in the individual slice images. Therefore, the average Hmp of the subcutaneous fat region ratios and the average Hmo of the visceral fat region ratios also take a value of zero or more and one or less.

Since the average Hmp of the subcutaneous fat region ratios is obtained by sampling the slice images that represent three different cross-sections of the abdominal area, it can be considered as a value that approximates the ratio of the volume of the entire subcutaneous fat region in the abdominal area to the volume of the entire abdominal area (volume ratio).

In other words, this can prevent these ratios from being a singular value due to uneven distribution of the subcutaneous fat region and/or the visceral fat region in the abdominal area. That is, an averaging effect can be obtained by increasing the number of samples. Thus, the average values of the subcutaneous fat region ratios and the visceral fat region ratios obtained from the more than one slice images representing different cross-sections have smaller fluctuation than a subcutaneous fat region ratio and a visceral fat region ratio that are obtained from a single slice image representing one cross-section.

Then, the average Hmp of the subcutaneous fat region ratios and the average Hmo of the visceral fat region ratios are summed up to obtain a body fat region ratio Hmb ($Hmb=Hmp+Hmo$). The body fat region ratio Hmb represents a ratio of the sizes of the subcutaneous fat region and the visceral fat region in the abdominal area to the size of the abdominal area for the slice images G1-G3. That is, the body fat region ratio Hmb represents a ratio of the summed size of the subcutaneous fat region and the visceral fat region in the abdominal area to the size of the abdominal area.

It should be noted that the body fat region is a combined region of the visceral fat region and the subcutaneous fat region.

Subsequently, as shown in FIG. 4, the body fat region ratio Hmb of the subject H is compared with a body fat region ratio Mmb of the human body model M, which corresponds to the body fat region ratio Hmb, to acquire the index which indicates a condition of obesity of the subject H.

The body fat region ratio Mmb of the human body model M represents a ratio of the sizes of the subcutaneous fat region and the visceral fat region in the abdominal area to the size of the abdominal area of the human body model M.

It should be noted that, although the human body model in this embodiment represents a human body with standard sizes and distributions of the abdominal area, the subcutaneous fat region and the visceral fat region, the human body model may represent an obese human body.

The body fat region ratio Mmb of the human body model M can be obtained using slice images representing three cross-sections M1-M3 of the human body model M that correspond to the three cross-sections H1-H3 of the subject H. That is, the body fat region ratio Mmb of the human body model M can be obtained by applying, to the slice images representing the cross-sections M1-M3, the same method for obtaining the body fat region ratio Hmb of the subject H.

Since the average Hmb of the body fat region ratios of the subject H can be considered as approximating the ratio of the volume of the entire body fat regions Fs in the abdominal area Hb to the volume of the entire abdominal area Hb of the subject H (volume ratio), as described above, the body fat region ratio of the human body model M may be a volume ratio. That is, a ratio of the volume of the entire body fat region in the abdominal area Mb to the volume of the entire abdominal area Mb of the human body model M (volume ratio) may be used as the body fat region ratio of the human body model M. This ratio (volume ratio) is an invariant value for the human body model M which is not influenced by the positions where the slice images are acquired.

Now, the index that indicates a condition of obesity of the subject H is explained. The index may be classified, for example, into one of three levels including: level 3 (dangerous); level 2 (potentially dangerous); and level 1 (normal). The indices of levels 1 to 3 are associated with results of comparison between the body fat region ratio Hmb of the subject H and the body fat region ratio Mmb of the human body model M.

A body fat comparison result value Jb representing a result of the comparison between the body fat region ratio Hmb of the subject H and the body fat region ratio Mmb of the human body model M is obtained in the following manner.

The value Jb representing the result of comparison of the body fat regions is obtained by dividing the body fat region ratio Hmb of the subject H with the body fat region ratio Mmb of the human body model M. The body fat comparison result value Jb is expressed by the equation:

body fat comparison result value $Jb$=body fat region ratio $Hmb$ of subject $H$/body fat region ratio $Mmb$ of human body model $M$.

If the body fat comparison result value Jb is "1", the body fat region ratio of the subject H and that of the human body model M are the same. The larger the value Jb, the larger the ratio of the body fat region Fs in the abdominal area Hb of the subject H than the corresponding ratio of the human body model M.

The body fat comparison result value Jb and the indices of levels 1 to 3 are associated as shown below, for example.

The index of level 1 (normal) corresponds to a range of: 0.5<the body fat comparison result value Jb≤1.5.

The index of level 2 (potentially dangerous) corresponds to a range of: 0.3<the body fat comparison result value Jb≤0.5, or 1.5<the body fat comparison result value Jb≤2.5.

The index of level 3 (dangerous) corresponds to a range of: the body fat comparison result value Jb≤0.3, or 2.5<the body fat comparison result value Jb.

Thus, the index indicating a condition of obesity of the subject can be obtained from the body fat comparison result value Jb obtained from the comparison between the body fat region ratio of the subject H and the body fat region ratio of the human body model M and the above-described correspondence between the body fat comparison result value Jb and the indices.

For example, if the body fat result comparison value Jb is 1.7, the index corresponding to the value is level 2 (potentially dangerous).

Figure 5:
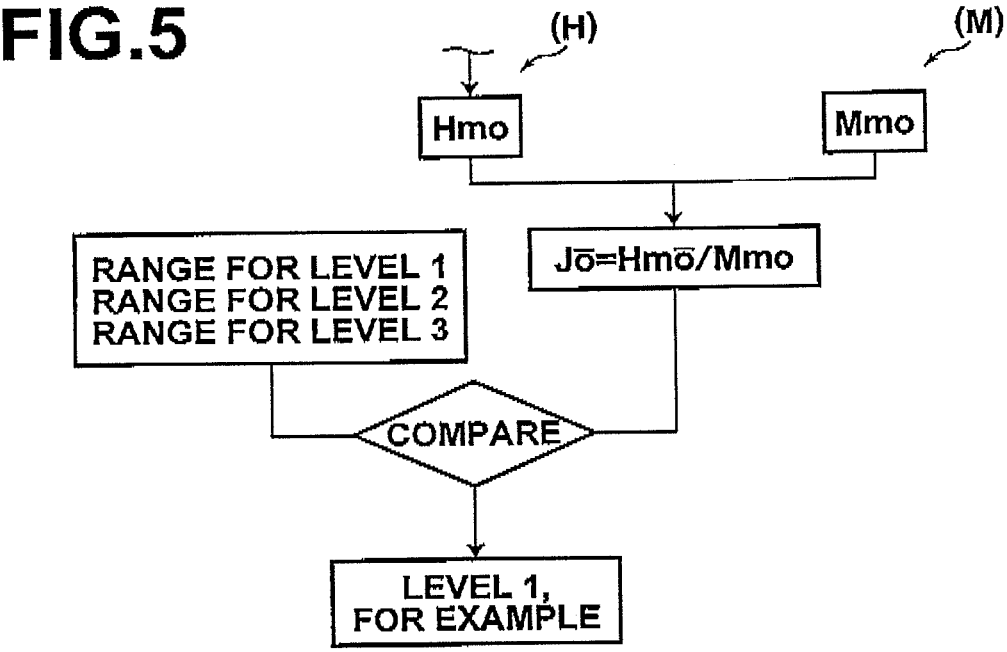
FIG. 5 is a flow chart of a second embodiment of the process to acquire the diagnostic index indicating a condition of obesity of the subject, which acquires the index based on a size of a visceral fat region of the subject.

Next, a second embodiment of the invention will be described with reference to FIG. 5. FIG. 5 is a flow chart of a process to acquire the index indicating a condition of obesity of the subject H from the size of the visceral fat region Fo of the subject H.

In the second embodiment, the slice images representing two or more cross-sections of the abdominal area of the subject are prepared, and a size of a normalized visceral fat region is calculated for each slice image. Then, the size of the normalized visceral fat region of the subject is compared with a size of the normalized visceral fat region of the human body model, which has been obtained in advance, to acquire the index indicating a condition of obesity of the subject. The size of the normalized visceral fat region may, for example, be a ratio of the size of the visceral fat region in the abdominal area to the size of the abdominal area.

It should be noted that the method of acquiring the index indicating a condition of obesity from the size of the normalized visceral fat region of the second embodiment is applicable to the method of the first embodiment.

First, similarly to the first embodiment, the average Hmo of the visceral fat region ratios of the subject H is calculated.

In the following explanation, the index indicating a condition of obesity of the subject H is acquired by comparing the average Hmo of the visceral fat region ratios of the subject H with the corresponding visceral fat region ratio Mmo of the human body model M, which has been determined in advance.

The size of the normalized visceral fat region of the human body model M may be a ratio of the size of the visceral fat region in the abdominal area to the size of the abdominal area of the human body model M, i.e., the visceral fat region ratio.

Similarly to the above-described first embodiment, the average Hmo of the visceral fat region ratios of the subject H is a value obtained from the slice images representing three different cross-sections of the abdominal area. Therefore, it can be considered as a value that approximates the ratio of the volume of the entire visceral fat region in the abdominal area to the volume of the entire abdominal area.

The visceral fat region ratio Mmo of the human body model M can be obtained from the slice images representing the three cross-sections M1-M3 of the abdominal area Mb of the human body model M, which correspond to the three cross-sections H1-H3 of the abdominal area Hb of the subject H, in the same manner for obtaining the visceral fat region ratio Hmo of the subject H described above.

Since the average Hmo of the visceral fat region ratios of the subject H can be considered as approximating the ratio of the volume of the entire visceral fat region Fo in the abdominal area Hb to the volume of the entire abdominal area Hb of the subject H, as described above, the visceral fat region ratio of the human body model M may be a volume ratio. That is, a ratio of the volume of the entire visceral fat region in the abdominal area Mb to the volume of the entire abdominal area Mb of the human body model M (volume ratio) may be used as the visceral fat region ratio of the human body model M. This ratio (volume ratio) is an invariant value for the human body model M which is not influenced by the positions where the slice images are acquired.

Now, the index that indicates a condition of obesity of the subject H is explained. The index may be classified, for example, into one of three levels including: level 3 (dangerous); level 2 (potentially dangerous); and level 1 (normal). The indices of levels 1 to 3 are associated with results of comparison between the visceral fat region ratio Hmo of the subject H and the visceral fat region ratio Mmo of the human body model M.

A visceral fat comparison result value Jo representing a result of the comparison between the visceral fat region ratio Hmo of the subject H and the visceral fat region ratio Mmo of the human body model M can be acquired in the following manner.

The value Jo representing the result of comparison between the visceral fat regions is acquired by dividing the average Hmo of the visceral fat region ratios of the subject H by the visceral fat region ratio Mmo of the human body model M. The visceral fat comparison result value Jo is expressed by the equation:

visceral fat comparison result value $Jo$=average $Hmo$ of visceral fat region ratios/visceral fat region ratio $Mmo$.

If the visceral fat comparison result value Jo is "1", the visceral fat region ratio of the subject H and the visceral fat region ratio of the human body model M are the same. The larger the value Jo, the larger the ratio of the visceral fat region Fo to the abdominal area Hb of the subject H.

The visceral fat comparison result value Jo and the indices of levels 1 to 3 are associated as shown below, for example.

The index of level 1 (normal) corresponds to a range of: $0.6 <$ the visceral fat comparison result value $Jo \leq 1.4$.

The index of level 2 (potentially dangerous) corresponds to a range of: $0.4 <$ the visceral fat comparison result value $Jo \leq 0.6$, or $1.4 <$ the visceral fat comparison result value $Jo \leq 2.0$.

The index of level 3 (dangerous) corresponds to a range of: the visceral fat comparison result value $Jo \leq 0.4$, or $2.0 <$ the visceral fat comparison result value Jo.

Thus, the index indicating a condition of obesity of the subject can be obtained from the visceral fat comparison result value Jo obtained from the comparison between the visceral fat region ratio of the subject H and the visceral fat region ratio of the human body model M and the above-described correspondence between the visceral fat comparison result value Jo and the indices.

For example, if the visceral fat result comparison value Jo of the subject H is 1.3, the index corresponding to the value is level 1 (normal).

Figure 6:
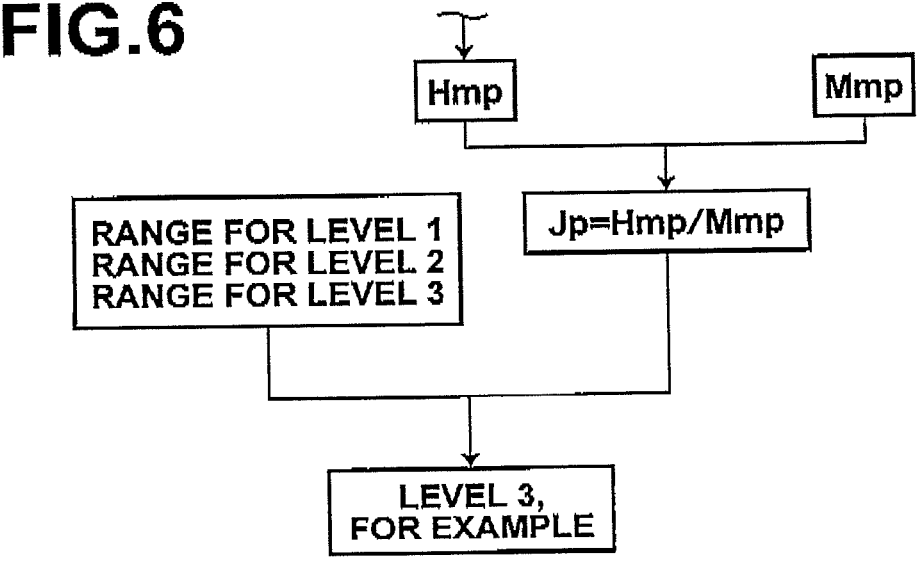
FIG. 6 is a flow chart of a third embodiment of the process to acquire the diagnostic index indicating a condition of obesity of the subject, which acquires the index based on a size of a subcutaneous fat region of the subject.

Next, a third embodiment of the invention will be described. FIG. 6 is a flow chart of a process to acquire the index indicating a condition of obesity of the subject H from the size of the subcutaneous fat region Fp of the subject H.

In the third embodiment, the slice images representing two or more cross-sections of the abdominal area of the subject are prepared, and a size of a normalized subcutaneous fat region is calculated for each slice image. Then, the size of the normalized subcutaneous fat region of the subject is compared with a size of the normalized subcutaneous fat region of the human body model, which has been obtained in advance, to acquire the index indicating a condition of obesity of the subject. The size of the normalized subcutaneous fat region may, for example, be a ratio of the size of the subcutaneous fat region in the abdominal area to the size of the abdominal area.

It should be noted that the method of acquiring the index indicating a condition of obesity from the size of the normalized subcutaneous fat region of the third embodiment is applicable to the method of the first embodiment.

First, similarly to the first embodiment, the average Hmp of the of subcutaneous fat region ratios of the subject H is calculated.

In the following explanation, the index indicating a condition of obesity of the subject H is acquired by comparing the average Hmp of the subcutaneous fat region ratios of the subject H with the corresponding subcutaneous fat region ratio Mmp of the human body model M, which has been determined in advance.

The subcutaneous fat region ratio Map of the human body model M represents a ratio the size of the subcutaneous fat region in the abdominal area to the size of the abdominal area of the human body model M.

Since the average Hmp of the subcutaneous fat region ratios is a value obtained from the slice images representing three different cross-sections of the abdominal area, it can be considered as a value that approximates the ratio of the volume of the entire subcutaneous fat region in the abdominal area to the volume of the entire abdominal area.

The subcutaneous fat region ratio Mmp of the human body model M can be obtained from the slice images representing the three cross-sections M1-M3 of the abdominal area Mb of the human body model M, which correspond to the three cross-sections H1-H3 of the abdominal area Hb of the subject H, in the same manner for obtaining the subcutaneous fat region ratio Hmp of the subject H described above.

Since the average Hmp of the subcutaneous fat region ratios of the subject H can be considered as approximating the ratio of the volume of the entire subcutaneous fat region Fp in the abdominal area Hb to the volume of the entire abdominal area Hb of the subject H, as described above, the subcutaneous fat region ratio of the human body model M may be a volume ratio. That is, a ratio of the volume of the entire subcutaneous fat region in the abdominal area Mb to the volume of the entire abdominal area Mb of the human body model M (volume ratio) may be used as the subcutaneous fat region ratio Mmp of the human body model M. This ratio (volume ratio) is an invariant value for the human body model M which is not influenced by the positions where the slice images are acquired.

Now, the index that indicates a condition of obesity of the subject H is explained. The index may be classified, for example, into one of three levels including: level 3 (dangerous); level 2 (potentially dangerous); and level 1 (normal). The indices of levels 1 to 3 are associated with results of comparison between the average Hmp of the subcutaneous fat region ratios of the subject H and the subcutaneous fat region ratio Mmp of the human body model M.

A subcutaneous fat comparison result value Jp representing a result of the comparison between the average Hmp of the subcutaneous fat region ratios of the subject H and the subcutaneous fat region ratio Mmp of the human body model M is acquired in the following manner.

The value Jp representing the result of comparison between the subcutaneous fat regions is acquired by dividing the average Hmp of the subcutaneous fat region ratios of the subject H by the subcutaneous fat region ratio Mmp of the human body model M. The subcutaneous fat comparison result value Jp is expressed by the equation:

subcutaneous fat comparison result value $Jp$=average $Hmp$ of subcutaneous fat region ratios/subcutaneous fat region ratio $Mmp$.

If the subcutaneous fat comparison result value Jp is "1", the subcutaneous fat region ratio of the subject H and the subcutaneous fat region ratio of the human body model M are the same. The larger the value Jp, the larger the ratio of the subcutaneous fat region Fp to the abdominal area Hb of the subject H.

The subcutaneous fat comparison result value Jp and the indices of levels 1 to 3 are associated as shown below, for example.

The index of level 1 (normal) corresponds to a range of: $0.7 <$ the subcutaneous fat comparison result value $Jp \leq 1.5$.

The index of level 2 (potentially dangerous) corresponds to a range of: $0.3 <$ the subcutaneous fat comparison result value $Jp \leq 0.7$, or $1.5 <$ the subcutaneous fat comparison result value $Jp \leq 2.2$.

The index of level 3 (dangerous) corresponds to a range of: the subcutaneous fat comparison result value $Jp \leq 0.3$, or $2.2 <$ the subcutaneous fat comparison result value Jp.

Thus, the index indicating a condition of obesity of the subject can be obtained from the subcutaneous fat comparison result value Jp obtained from the comparison between the subcutaneous fat region ratio of the subject H and the subcutaneous fat region ratio of the human body model M and the above-described correspondence between the subcutaneous fat comparison result value Jp and the indices.

For example, it the subcutaneous fat result comparison value J of the subject H is 2.5, the index corresponding to the value is level 3 (dangerous).

Figure 7:
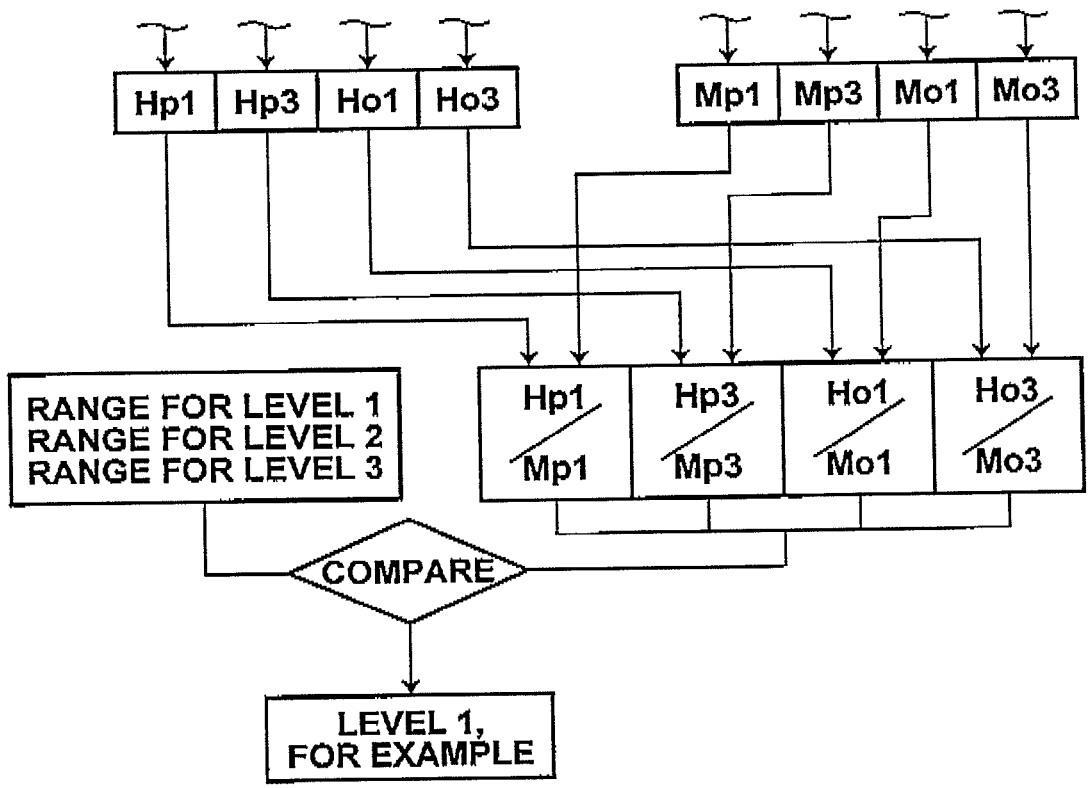
FIG. 7 is a flow chart of a fourth embodiment of the process to acquire the diagnostic index indicating a condition of obesity of the subject, which acquires the index based on sizes of the subcutaneous fat region and a visceral fat region of the subject.

Next, a fourth embodiment of the invention will be described with reference to FIG. 7. FIG. 7 is a flow chart of a process to acquire the index indicating a condition of obesity of the subject H from the sizes of the subcutaneous fat region Fp and the visceral fat region Fo of the subject H.

In the fourth embodiment, slice images representing two or more cross-sections of the abdominal area of the subject are prepared, and a ratio of the sizes of the subcutaneous fat region and the visceral fat region in the abdominal area to the abdominal area is calculated for each slice image. Then, the above ratio of the subject is compared with the corresponding ratio of the human body model, which has been obtained in advance, to acquire the index indicating a condition of obesity of the subject. This is one example of the method of acquiring a diagnostic index which is similar to the method of the first embodiment.

In the fourth embodiment, the slice images include a slice image that represents a cross-section which is nearer to the head than a cross-section crossing a substantial center of the abdominal area and being orthogonal to the body height direction (the direction of arrow Z in the drawing), and a slice image that represents a cross-section which is nearer to the legs than the cross-section crossing the substantial center of the abdominal area. The cross-section crossing the substantial center of the abdominal area may be a cross-section that crosses the umbilicus of the subject.

First, similarly to the first embodiment, the subcutaneous fat region ratios Hp1 and Hp3 and the visceral fat region ratios Ho1 and Ho3 of the subject H are calculated.

The subcutaneous fat region ratio Hp1 and the visceral fat region ratio Ho1 are values calculated for the slice image that represents the cross-section which is nearer to the head than the cross-section crossing the substantial center of the abdominal area and being orthogonal to the body height direction. The subcutaneous fat region ratio Hp3 and the visceral fat region ratio Ho3 are values calculated for the slice image that represents the cross-section which is nearer to the legs than the cross-section crossing the substantial center of the abdominal area and being orthogonal to the body height direction.

Now, explanation is given on a case where the index indicating a condition of obesity of the subject H is acquired by comparing the subcutaneous fat region ratios Hp1, Hp3 and the visceral fat region ratios Ho1, Ho3 of the subject H with corresponding subcutaneous fat region ratios Mp1, Mp3 and visceral fat region ratios Mo1, Mo3 of the human body model M, which have been determined in advance.

The index may be classified, for example, into one of three levels including: level 3 (dangerous); level 2 (potentially dangerous); and level 1 (normal). The indices of levels 1 to 3 are associated with results of the comparison of the subcutaneous fat region ratios Hp1, Hp3 and the visceral fat region ratios Ho1, Ho3 of the subject H with the subcutaneous fat region ratios Mp1, Mp3 and the visceral fat region ratios Mo1, Mo3 of the human body model M.

The subcutaneous and visceral fat comparison result values Jop which respectively represent the results of the comparison between the values Hp1, Hp3, Ho1 and Ho3 of the subject H and the values Mp1, Mp3, Mo1 and Mo3 of the human body model M are obtained in the following manner.

Values Jp1, Jp3, Jo1 and Jo3 respectively representing the subcutaneous and visceral fat comparison results are obtained by dividing each of the values Hp1, Hp3, Ho1 and Ho3 of the subject H with corresponding one of the values Mp1, Mp3, Mo1 and Mo3 of the human body model M.

The value Jp1, Jp3, Jo1 and Jo3 representing the subcutaneous and visceral fat comparison results are expressed by the equations: Jp1=Hp1/Mp1; Jp3=Hp3/Mp3; Jo1=Ho1/Mo1; and Jo3=Ho3/Mo3. If the subcutaneous or visceral fat comparison result value is "1", the ratio of the fat of the subject H and the ratio of the corresponding fat of the human body model M is the same. The larger the value, the larger the ratio of the visceral fat region Fo or the subcutaneous fat region Fp in the abdominal area Hb.

The subcutaneous and visceral fat comparison result values Jp1, Jp3, Jo1 and Jo3 and the indices of levels 1 to 3 are associated as shown below, for example.

The index of level 1 (normal) corresponds to a case where each of the values Jp1, Jp3, Jo1 and Jo3 is within a range of more than 0.6 and not more than 1.5.

The index of level 2 (potentially dangerous) corresponds to a case where each of the values Jp1, Jp3, Jo1 and Jo3 is within a range of more than 0.2 and less than 0.6, or more than 1.5 and not more than 2.5.

The index of level 3 (dangerous) corresponds to a case where each of the values Jp1, Jp3, Jo1 and Jo3 is within a range of less than 0.2 or more than 2.5.

Thus, the index indicating a condition of obesity of the subject can be obtained from the visceral and subcutaneous fat comparison result values obtained by comparing the visceral fat region ratios and the subcutaneous fat region ratios of the subject H with those of the human body model M, and the above-described correspondence between the visceral and subcutaneous fat comparison result values and the indices.

For example, if each of the visceral and subcutaneous fat result comparison values Jp1, Jp3, Jo1 and Jo3 of the subject H is 0.7, the index corresponding to the value is level 1 (normal).

The slice images may be taken more than once in time-series, and the index may indicate a change in the condition of obesity over time. Now, explanation is given on a case where the diagnostic index is acquired using the slice images that have been taken more than once in time-series.

The slice images representing two or more cross-sections in the abdominal area of the subject are taken more than once in time-series, i.e., in the order of date t1, date t2, date t3, . . . . Then, for the slice images of the respective dates t1, t2, t3, . . . , time-series indices are acquired according to any of the methods described in the first to fourth embodiments. In this example, the index for the date t1 is level 2, the index for the date t2 is level 2, the index for the date t3 is level 1, and the index for the date t4 is level 2. In this manner, the time-series indices (t1: level 2, t2: level 2, t3: level 1, and t4: level 2) are acquired. By comparing the thus acquired time-series indices with predetermined ranges for the time-series indices, a time-series diagnostic index indicating a change in the condition of obesity over time can be acquired. Examples of the diagnostic index may include: category X1—the body fat decreasing; category X2—no change in the body fat; and category X3—the body fat increasing, or category Y1—the visceral fat increasing; category Y2—the subcutaneous fat decreasing; and the like.

Although it is preferred that the slice images of the abdominal area represent cross-sections that are orthogonal to the body height direction of the subject (the direction along the spine), this is not intended to limit the invention, and the slice images may represent cross-sections that are oblique to the body height direction of the subject.

Further, the abdominal area of the subject may be an area between a cross-section that crosses any one of the periphery of the upper portion of the liver, the lower portion of the diaphragm and the intervertebral portion of the spine and is orthogonal to the body height direction of the subject, and a cross-section that crosses any one of the upper portion of the ilium bone, the lower portion of the ilium bone and the lower portion of the sacrum bone and is orthogonal to the body height direction of the subject.

According to the method of acquiring a diagnostic index of the invention, a ratio of the size of the subcutaneous fat region and/or the visceral fat region in the abdominal area to the abdominal area is obtained from the slice images representing two or more cross-sections of the abdominal area of the subject, and the ratio obtained for the subject is compared with the corresponding ratio obtained in advance for the human body model to acquire the diagnostic index indicating a condition of obesity of the subject. The thus acquired diagnostic index has improved reliability as an indication of a condition of obesity of the subject.

That is, since the ratio of the size of the subcutaneous fat region and/or the visceral fat region is calculated from the slice images that represent two or more cross-sections crossing different positions of the abdominal area of the subject, the larger number of slice image samples are used to acquire the diagnostic index than a case where the ratio is calculated from a single slice image representing one cross-section. This provides an averaging effect due to increase in the number of samples. Thus, fluctuation of the calculated ratio due to differences among individuals, such as differences in distribution of fat and/or positions of organs, can be reduced, thereby reducing discrepancy in the diagnostic indices due to differences in body structures of individual subjects. In this manner, reliability of the diagnostic index indicating a condition of obesity of the subject can be improved.

Further, in an aspect of the invention where the slice images are taken more than once in time-series and the diagnostic index indicates a change in the condition of obesity over time, the diagnostic index can be acquired based on more information indicating the condition of obesity of the subject. Thus, reliability of the diagnostic index indicating the condition of obesity of the subject can further be improved.

Furthermore, in an aspect of the invention where the slice images include a slice image representing a cross-section nearer to a head of the subject than a cross-section crossing an umbilicus of the subject and being orthogonal to a body height direction of the subject, and a slice image representing a cross-section nearer to legs of the subject than the cross-section crossing the umbilicus, deviation of sampling positions of the slice images to be used can be reduced, and this can reduce influences of differences in distribution of the fat and positions of the organs due to differences among individuals. In this manner, discrepancy in the diagnostic indices due to differences in body structures of individual subjects can be reduced, and reliability of the diagnostic index indicating the condition of obesity of the subject can further be improved.

What is claimed is:

1. A diagnostic index acquiring apparatus for acquiring diagnostic indices with respect to body fat of a subject, comprising:

means for preparing slice images representing two or more cross-sections of an abdominal area of the subject;

means for obtaining, for each of the two or more slice images, a size of a subcutaneous fat region and a size of a visceral fat region in the abdominal area; and means for calculating a diagnostic index related to the body fat of the subject by combining an average value of the size of the subcutaneous fat region and an average value of the size of the visceral fat region based on the two or more slice images.

2. A diagnostic index acquiring apparatus as defined in claim 1, wherein:

the means for calculating the diagnostic index obtains the diagnostic index by comparing the average values for the subcutaneous fat and visceral fat regions of the at least two slice images of the subject and reference average values related to a human model which are not related to the subject from which the at least two slice images are taken.

3. A diagnostic index acquiring apparatus as defined in claim 2, wherein:

the size of the subcutaneous fat region is a normalized value represented as a ratio of a cross-sectional area of the subcutaneous fat region with respect to a cross-sectional area of the abdominal area in each of the of at least two slice images taken of the subject; and the size of the visceral fat region is a normalized value represented as a ratio of a cross-sectional area of the visceral fat region with respect to a cross-sectional area of the abdominal area in each of the at least two slice images taken of the subject.

4. A diagnostic index acquiring apparatus as defined in claim 3, wherein:

the slice images are taken more than once in time series; and the diagnostic index indicates a change in a condition of obesity over time.

5. A diagnostic index acquiring apparatus as defined in claim 4, wherein:

the slice images comprise a slice image representing a cross-section nearer to a head of the subject than a cross-section crossing an umbilicus of the subject and being orthogonal to a body height direction of the subject, and a slice image representing a cross-section nearer to legs of the subject than the cross-section crossing the umbilicus.

6. A diagnostic index acquiring apparatus as defined in claim 3, wherein:

the slice images comprise a slice image representing a cross-section nearer to a head of the subject than a cross-section crossing an umbilicus of the subject and being orthogonal to a body height direction of the subject, and a slice image representing a cross-section nearer to legs of the subject than the cross-section crossing the umbilicus.

7. A diagnostic index acquiring apparatus as defined in claim 2, wherein:

the slice images are taken more than once in time series; and the diagnostic index indicates a change in a condition of obesity over time.

8. A diagnostic index acquiring apparatus as defined in claim 7, wherein:

the slice images comprise a slice image representing a cross-section nearer to a head of the subject than a cross-section crossing an umbilicus of the subject and being orthogonal to a body height direction of the subject, and a slice image representing a cross-section nearer to legs of the subject than the cross-section crossing the umbilicus.

9. A diagnostic index acquiring apparatus as defined in claim 2, wherein:
the slice images comprise a slice image representing a cross-section nearer to a head of the subject than a cross-section crossing an umbilicus of the subject and being orthogonal to a body height direction of the subject, and a slice image representing a cross-section nearer to legs of the subject than the cross-section crossing the umbilicus.

10. A diagnostic index acquiring apparatus as defined in claim 1, wherein:
the size of the subcutaneous fat region is a normalized value represented as a ratio of a cross-sectional area of the subcutaneous fat region with respect to a cross-sectional area of the abdominal area in each of the at least two slice images taken of the subject; and
the size of the visceral fat region is a normalized value represented as a ratio of a cross-sectional area of the visceral fat region with respect to a cross-sectional area of the abdominal area in each of the at least two slice images taken of the subject.

11. A diagnostic index acquiring apparatus as defined in claim 10, wherein:
the slice images are taken more than once in time series; and
the diagnostic index indicates a change in a condition of obesity over time.

12. A diagnostic index acquiring apparatus as defined in claim 10, wherein:
the slice images comprise a slice image representing a cross-section nearer to a head of the subject than a cross-section crossing an umbilicus of the subject and being orthogonal to a body height direction of the subject, and a slice image representing a cross-section nearer to legs of the subject than the cross-section crossing the umbilicus.

13. A diagnostic index acquiring apparatus as defined in claim 11, wherein:
the slice images comprise a slice image representing a cross-section nearer to a head of the subject than a cross-section crossing an umbilicus of the subject and being orthogonal to a body height direction of the subject, and a slice image representing a cross-section nearer to legs of the subject than the cross-section crossing the umbilicus.

14. The apparatus of claim 10, wherein the means for calculating the diagnostic index calculates a value representing a volume ratio of fat of the abdominal area of the subject, said volume ratio being determined based on the at least two slice images taken of the subject.

15. The apparatus of claim 14, wherein the means for calculating the diagnostic image calculates a single volume ratio based on at least one of: the normalized value represented as the ratio in relation to the subcutaneous fat region and the normalized value represented as the ratio in relation to the visceral fat region.

16. The apparatus of claim 15, wherein the normalized value represented as the ratio in relation to the subcutaneous fat region (Hp) and the normalized value represented as the ratio in relation to the visceral fat region (Ho) satisfy $0 \leq Hp \leq 1$ and $0 \leq Ho \leq 1$.

17. The apparatus of claim 15, wherein the single volume ratio is the sum of the normalized value represented as the ratio in relation to the subcutaneous fat region and the normalized value represented as the ratio in relation to the visceral fat region.

18. The apparatus of claim 17, wherein the normalized value represented as the ratio in relation to the subcutaneous fat region (Hp) and the normalized value represented as the ratio in relation to the visceral fat region (Ho) satisfy $0 \leq Hp \leq 1$ and $0 \leq Ho \leq 1$.

19. A diagnostic index acquiring apparatus as defined in claim 1, wherein:
the slice images are taken more than once in time series; and
the diagnostic index indicates a change in a condition of obesity over time.

20. A diagnostic index acquiring apparatus as defined in claim 19, wherein:
the slice images comprise a slice image representing a cross-section nearer to a head of the subject than a cross-section crossing an umbilicus of the subject and being orthogonal to a body height direction of the subject, and a slice image representing a cross-section nearer to legs of the subject than the cross-section crossing the umbilicus.

21. A diagnostic index acquiring apparatus as defined in claim 1, wherein:
the slice images comprise a slice image representing a cross-section nearer to a head of the subject than a cross-section crossing an umbilicus of the subject and being orthogonal to a body height direction of the subject, and a slice image representing a cross-section nearer to legs of the subject than the cross-section crossing the umbilicus.

22. A diagnostic index acquiring apparatus as defined in claim 1, wherein:
each of the cross-sections of the abdominal area of the subject comprises a cross-section orthogonal to a body height direction of the subject.

* * * * *